(12) United States Patent  
Williams

(10) Patent No.: US 6,723,061 B2
(45) Date of Patent: Apr. 20, 2004

(54) DYNAMIC SPLINT FOR CARPAL TUNNEL SYNDROME TREATMENT

(76) Inventor: George Roger Williams, 3024 SE. 40th, Edmond, OK (US) 73013

( * ) Notice: Subject to any disclaimer, the term of this patent is extended or adjusted under 35 U.S.C. 154(b) by 0 days.

(21) Appl. No.: 09/998,850

(22) Filed: Nov. 23, 2001

(65) Prior Publication Data

US 2002/0035342 A1 Mar. 21, 2002

Related U.S. Application Data

(63) Continuation-in-part of application No. 09/391,577, filed on Sep. 8, 1999, now abandoned.
(60) Provisional application No. 60/099,358, filed on Sep. 8, 1998, and provisional application No. 60/137,679, filed on Jun. 4, 1999.

(51) Int. Cl.$^7$ .................................................. A61F 5/00
(52) U.S. Cl. .......................................... 602/21; 602/16
(58) Field of Search ........................... 602/21, 20, 22, 602/5, 60–64, 19, 16, 23; 482/45, 44, 46; 601/40

(56) References Cited

U.S. PATENT DOCUMENTS

| 3,124,127 | A | * | 3/1964 | Ruuska ........................ 602/21 |
|---|---|---|---|---|
| 3,269,728 | A | * | 8/1966 | Blough ........................ 473/62 |
| 3,299,887 | A | * | 1/1967 | Czap ........................... 602/21 |
| 4,220,334 | A | * | 9/1980 | Kanamoto et al. ............ 482/48 |
| 4,294,237 | A | * | 10/1981 | Frazier ......................... 602/21 |
| 4,441,489 | A | * | 4/1984 | Evans et al. .................. 602/22 |
| 4,657,000 | A | | 4/1987 | Hepburn |
| 4,662,364 | A | * | 5/1987 | Viegas et al. ................. 602/21 |
| 4,665,905 | A | * | 5/1987 | Brown ......................... 602/16 |
| 4,677,971 | A | * | 7/1987 | Lindemann .................. 602/21 |
| 4,772,012 | A | | 9/1988 | Chesher |
| 4,809,688 | A | * | 3/1989 | Aymerica del Valle et al. ............................ 602/21 |
| 4,862,877 | A | | 9/1989 | Barber |
| 4,928,677 | A | * | 5/1990 | Barber ......................... 602/21 |
| 4,941,460 | A | * | 7/1990 | Working ...................... 602/21 |
| 5,002,044 | A | | 3/1991 | Carter |
| 5,205,812 | A | | 4/1993 | Wasserman |
| 5,279,545 | A | * | 1/1994 | Reese, Sr. .................... 602/21 |
| 5,350,418 | A | * | 9/1994 | Janevski et al. ............. 607/111 |
| 5,417,645 | A | | 5/1995 | Lemmen |
| 5,653,680 | A | * | 8/1997 | Cruz ............................ 602/21 |
| 5,685,013 | A | * | 11/1997 | Hausman ....................... 2/16 |
| 5,695,453 | A | * | 12/1997 | Neal .............................. 602/6 |
| 5,702,355 | A | | 12/1997 | Repice et al. |
| 5,759,165 | A | * | 6/1998 | Malewicz .................... 602/21 |
| 5,759,166 | A | * | 6/1998 | Nelson et al. ............... 602/21 |
| 5,778,449 | A | * | 7/1998 | Oetting et al. ................ 2/16 |
| 5,868,692 | A | | 2/1999 | Michniewicz |
| 5,971,945 | A | | 10/1999 | Garris |
| 6,163,885 | A | * | 12/2000 | Webb ........................... 2/166 |
| 6,238,358 | B1 | * | 5/2001 | Philot et al. ................... 602/5 |

* cited by examiner

Primary Examiner—Nicholas D. Lucchesi
Assistant Examiner—Huong Q. Pham
(74) Attorney, Agent, or Firm—James F. Harvey, III

(57) ABSTRACT

A method and appliance for the application of a continuous, low level force tending to oppose rotational movement of the hand about the carpus. This opposing force tends to relieve contractatures of the transverse carpal, volar carpal, and intra carpal ligaments over time, thus relieving the pain caused by carpal tunnel syndrome and correcting altered kinematics associated therewith. This opposing force tends to increase the carpal volume. According to the principles of the invention, a dynamic splint appliance is described which provides free movement of the patient's wrist with minimal impediment during activities of daily living, both at home and at work, while simultaneously applying this opposing force. The appliance consists of a forearm component to maintain alignment and to provide support and stabilization for a biasing means positioned on the ulnar side of the forearm, the biasing means consisting of a double coil spring located at approximately the ulnar side of the carpus and connected to a palmar component fastened to the ulnar side of the hand. The biasing component provides resistive force to volar glide in a manner which accurately models the kinematics of the carpus and forearm.

29 Claims, 10 Drawing Sheets

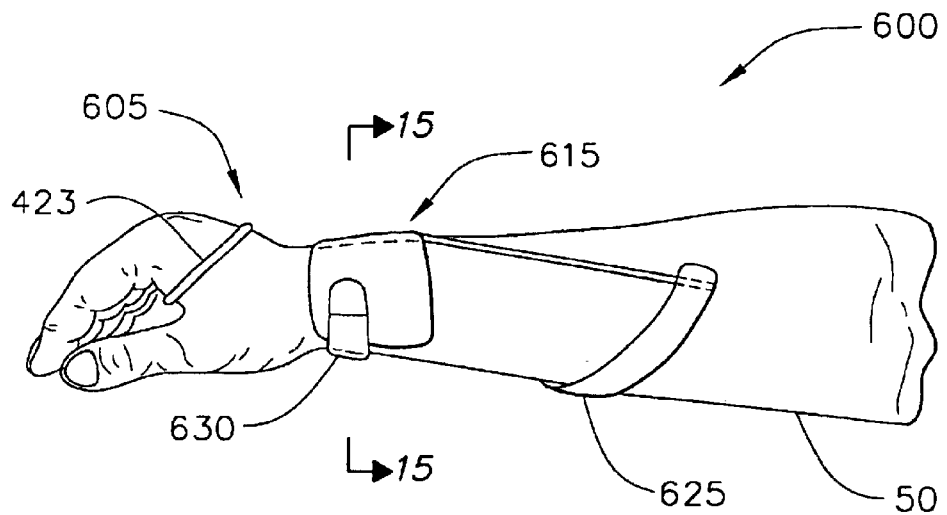
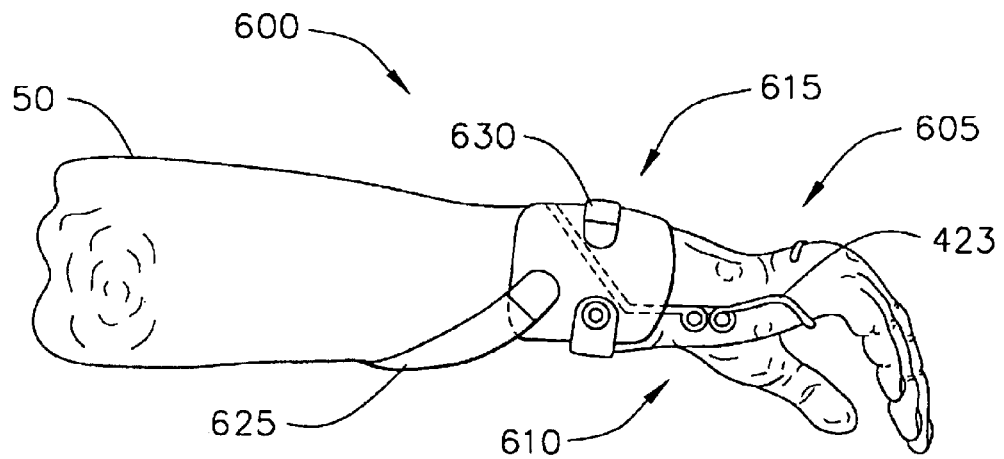

DYNAMIC SPLINT FOR CARPAL TUNNEL SYNDROME TREATMENT

This application is a continuation-in-part of U.S. patent application Ser. No. 09/391,577, filed on Sep. 8, 1999, now abandoned, and thereby claims the benefit of the provisional application No. 60/099,358, filed Sep. 8, 1998, and No. 60/137,679, filed on Jun. 4, 1999.

BACKGROUND OF THE INVENTION

1. Field of the Invention

The present invention relates generally to medical therapeutic systems, and deals more particularly with methods and devices for treating and curing functional disorders of the human carpus. More particularly, the present invention provides a splint for providing dynamic pressure to the transverse carpal, volar carpal, and intra-carpal ligaments, in a manner tending to relieve contractures of these ligaments and thus relieve the pain caused thereby.

2. Description of the Related Art

A. General Description of the Condition

Carpal tunnel syndrome (CTS) is a painful condition caused by compression of the median nerve of the forearm. The median nerve and the flexor tendons pass from the forearm to the hand through the wrist canal, or carpal tunnel. The median nerve in particular can be compressed by one or more factors such as a reduction in carpal tunnel volume or swelling of tissues passing through the carpal tunnel. Such compression of the median nerve causes intense pain to the patient, often necessitating extended therapy or surgery to alleviate the problem.

It is commonly believed that CTS is caused by prolonged repetitive activity, such as holding the hand, wrist, and forearm in an awkward position for extended lengths of time while exerting the associated muscles. Prolonged exertion at a keyboard or manual labor are common, but by no means the only, associations with CTS. The direct cause of CTS is believed to be a biomechanical ligament imbalance in the volar carpal ligaments, where the term "volar" indicates a direction towards the palm of the hand as opposed to "dorsal" which indicates a direction towards the back of the hand. Specifically, this biomechanical imbalance of the ligaments is believed to comprise a thickening of the palmer transverse carpal ligament (PTCL, also known as the retinacular ligament), a thickening of the volar intracarpal ligaments, and contraction of an assortment of volar carpal ligaments.

B. Kinematics of the Carpal/Forearm Complex

The flexor muscle tendons of the forearm acting on the wrist, fingers, and thumb volarly exert a collective static force many times greater than the extensor muscle tendons acting dorsally to stabilize these same members. This interaction between the flexor muscles (antagonist) and the extensor muscles (agonist) is termed "cocontraction". Cocontraction tends to hold the joint in a fixed and stable position. The flexor-to-extensor ratio of these opposing forces is normally four to one. However, work demands often increase this ratio through hypertrophy of the flexor muscle tendon units; this hypertrophy is caused by executing high intensity tasks involving extended duration and which dominantly involve finger, thumb, and wrist function.

The interaction between the carpal ligaments and the flexor and extensor muscles becomes more pronounced with time and intensity of activity. The effect of the volar flexor forces, acting upon the PTCL as a pulley, attenuate the PTCL and apply forces anteriorly and medially. This places traction forces to the ligament ends of the carpus. Each night, while the flexor/extensor muscles are at rest, the volar intracarpal ligaments restore their normal position grossly; however, some minute anteriomedial deformity remains, and slack of the PTCL is concurrently taken up by contractile forces of this and the other ligament(s). Numerous cycles of activity followed by rest develop an established deforming characteristic which is manifested by narrowing the horseshoe ends of the carpal tunnel, which are held in position by a thickening PTCL and other volar carpal ligaments, resulting in a transverse deformity. Simultaneously, the PTCL, acting as a pulley, concentrates the load of the finger and thumb function so that a volar glide is initiated, where volar glide is defined as movement of the carpal metacarpal complex as a unit in a volar direction. This volar glide of the carpal metacarpal complex attenuates the predisposed thin dorsal carpal ligaments (DCL) originating from the distal radial ulna (DRU). Since the volar carpal ligaments collectively become less stressed, they begin to contract, thus encouraging the anteriomedial collapse of the intercarpal spaces simultaneous to a longitudinal deformity.

The long moment arm of the carpal muscle tendon units are only capable of stabilization of the carpus when the muscle tone is within normal limits, i.e. flexor-to-extensor ration of approximately 4 to 1; these forces acting on the carpus in flexion are convergent toward the muscle origin and are regulated by an interplay of antagonists, pulleys, and joint alignment. A variation of one or more serves to simplify convergence towards a direct line to this point of origin and shorten the distance therebetween. This force results in a decreasing biomechanical advantage which is manifested by a volar shift of the axis of the proximal carpal row. This may account for the propensity of patients with CTS to develop odd compensatory behaviors as, for example, flexing the wrist during power grasping, conceivably to account for the change in position of the more volarly placed PTCL. Carpal tunnel volume is further reduced, and any other predisposition will hasten onset of the painful and crippling CTS condition. Thus, the resistance of the PTCL and related volar ligaments which is encountered when returning the carpal metacarpal complex to a neutral position, i.e. dorsal glide, should be indicative of the severity of the condition of carpal tunnel syndrome or the propensity of the subject to incur the condition.

C. Standard Treatment of Carpal Tunnel Syndrome

To date, CTS has been treated with wrist rests, antiinflammatory medications, cortisone injections, surgery, and static and dynamic wrist splints. Alone or combined, these treatments have met with varying degrees of minimal success. Symptom relief is short lived and compounded by surgical complications. Even after these treatments are applied, the patient's biomechanical configuration remains unchanged or complicated. Reduced grasp strength has been well documented. The obvious solution, i.e. removing the cause of the injury by refraining from the manual labor believed to cause the problem, is not always practical since the cause of the injury is frequently the means by which the patient obtains his or her livelihood. The next best choice, prevention through proper intervention, can be achieved by enlarging the carpal tunnel to maintain adequate space for the median nerve and thus avoid compression. However, the mechanism for correcting this condition long term does not yet exist.

The carpal tunnel can be enlarged by osteopathic manipulation and stretching maneuvers, thereby alleviating compression on the median nerve and resolving CTS. While severe cases may require other treatment, manipulation is effective in the majority of cases and has the advantage of being prophylactic, i.e. a preventative. Optimum resolution of the symptoms requires frequent stretching and the assistance of another person, a physician or therapist to perform the manipulation. There is a need for an appliance which a patient can use to augment treatment by the physician or therapist. It is known from studies of rehabilitated knee joints and elbow joints that the longest period of low force stretching produces the greatest amount of permanent elongation of connective tissue. Ideally, the stretching would be accomplished by means of an appliance which is adjusted by the physician or therapist to provide the appropriate force for stretching, preferably continuously.

The prior art is replete with splint appliances which are designed to reduce CTS pain. One such appliance is described in U.S. Pat. No. 5,417,645, issued to Lemmen, where a carpal splint is provided with an elongated, flexible member having a palmar portion configured to extend from the middle of the forearm, across the volar carpal area, and across the palm to bias the palm in a dorsal direction. It also functions as a reminder of the proper positioning to relieve pressure on the median nerve associated with CTS. It is designed to allow use of the fingers and thumb and to permit near normal hand function.

Another such appliance is described in a series of patents by Davini, i.e. U.S. Pat. Nos. 4,966,137, Re. 34,627, and 5,385,527. Each of these appliances is based upon essentially the same premise, namely, each functions to enlarge the carpal tunnel by compressing the radius and ulna together using an external clamp and bandage configuration which encircles the carpus, so that free use of the hand and fingers is permitted. Stretching of the PTCL or other carpal ligaments is not addressed by these devices.

Still another such appliance is described in U.S. Pat. No. 5,468,220, issued to Sucher. Like the '137 and '627 patents, it is also intended to relieve pressure on the median nerve by increasing the volume of the carpal tunnel. The appliance encircles the carpus and, using spring loaded pads, provides dorsal and volar pressure on the radius, ulna, and other carpal bones which tends to increase tunnel volume. It can be removed by the user if long term use causes irritation or sensitivity to the skin.

However, there are a number of difficulties in the use of such appliances. First, simply prescribing the use of an appliance does not mean that the patient will use it properly. If a patient is expected to put on and remove an appliance, a properly adjusted appliance must not be able to be put on incorrectly or to inflict either too much or too little stretching. Proper use also refers to the compliance or self-discipline of the patient and how easy it is to use the appliance. In general, an appliance that is mechanically simple, easy to use, and comfortable to wear will more likely be used as directed.

Second, the skin is sensitive to long term pressure, which can cause a localized loss of circulation and lead to ulceration. Obviously, a patient will not be comfortable if an appliance causes such irritation. On the other hand, sufficient pressure must be applied in order to be effective. Such an appliance must be comfortable to wear and not cause undue irritation or pressure on the skin.

Third, an appliance must not interfere with the normal activities of living. It must be comfortable in the sense that it does not interfere with the function of the arm, wrist, and hand. Otherwise, a patient is unlikely to wear the appliance long enough to be fully effective, preferably overnight, or when performing routine tasks which may irritate the median nerve or promote the deformities. An appliance duplicating the manipulation by a physician or therapist would obviously interfere with the patient's use of the hand. What is desired is an appliance which duplicates as much of the physician's treatment as possible without interfering with the use of the arm, wrist, or hand.

Fourth, it is desirable to have an appliance which will not only promote the stretching of the carpal ligaments so as to relieve pressure on the nerve, but also to restore the proper ratio of cocontraction between the flexor and extensor muscles which tend to hold the carpal joint in the proper alignment while carpal ligament stretching is being effected. This encouragement of cocontraction is missing from all existing devices. In order to achieve proper joint stabilization, the device must allow the ligaments to re-engage and reestablish joint stability as well as increasing muscle tone of the flexor and extensor muscles around the perimeter of the joint.

Fifth, it has been observed in practice that the distance between the metacarpals and the distal ulna-radius changes during flexion and extension of the hand. This change of distance results in an elliptical path being followed by the hand during its range of motion from flexion to extension. Furthermore, a differential motion has been observed during supination and pronation between the distal and proximal areas of the forearm. It is desirable in any dynamic splint design to mirror these kinematics so that binding of the appliance is prevented and a proper dorsal force can be applied by the splint appliance to resist volar glide.

Accordingly, what is needed is an improved appliance and method for resolving CTS. Such an appliance should desirably have the following characteristics:

1. The appliance must duplicate the stretching maneuver performed by a trained therapist to stretch the PTCL and collective volar carpal ligaments over time;
2. The appliance must be easily worn and removed by a patient with minimal or no training required for its use;
3. The appliance must not present pressure points to the patient or unduly irritate the skin;
4. The appliance must be easily worn during routine daily life with little or no interference with motion during supination and pronation or during manipulation of the fingers;
5. The appliance must both promote restoration of the carpal ligaments to their proper configuration as well as restore the proper cocontraction of the stabilizing flexor and extensor muscle groups against the carpal joint;
6. The appliance must be able to accommodate individuals having different forearm and wrist measurements; and,
7. The appliance must be not bind during supination and pronation of the forearm.

Other characteristics such as ease of manufacture and ease in cleaning the appliance are also desirable.

SUMMARY OF THE INVENTION

It is therefore an object of the present invention to provide an improved method and appliance for treating CTS.

It is another object of the invention to provide a method and appliance directed to the relief of pressure on the median nerve through the application of continuous, low intensity, volarly directed pressure to the hand in order to gradually lengthen the palmer transverse carpal ligament over time.

It is another object of the invention to provide a method and appliance which will restore the desired flexor-to-extensor ratio of force to the forearm of a person experiencing CTS.

It is a further object of the invention to provide a method and appliance which promotes restoration of the cocontractive forces of the flexor and extensor muscles on the carpal joint so as to allow the carpal ligaments to be properly stretched and/or contracted in order to achieve a normal carpal configuration.

Another object of the invention is to provide an appliance for the treatment of CTS which is comfortable to the person wearing the appliance.

Another object of the invention is to provide an appliance for the treatment of CTS which will not unduly interfere with the normal activities of daily living.

Another object of the invention is to provide an appliance which can be worn, adjustment, and removed by a patient with ordinary skill without adversely affecting the function of the appliance.

Another object of the invention is to provide an appliance which will not bind while the patient wearing the device performs supination or pronation movement and will continue to provide restorative force to the carpus during such movements.

Another object of the invention is to provide an appliance which is simple in construction.

Another object of the invention is to provide an appliance which can be easily adjusted to provide variable tension resisting dorsal movement of the hand.

Another object of the invention is to provide an appliance which accurately models the kinematics of the carpal/metacarpal complex in order to provide continuous tension resisting dorsal movement of the hand.

Other objects and advantages of the present invention will be set forth in part in the description and in the drawings which follow and, in part, will be obvious from the description or may be learned by practice of the invention.

To achieve the foregoing objects, and in accordance with the purpose of the invention as broadly described herein, the present invention provides methods and devices for a dynamic splint for relieving carpal tunnel syndrome. The method of the invention is implemented by means of a dynamic orthotic appliance designed to provide low level pressure on the PTCL over extended periods of time while at the same time allowing the user to execute the standard activities of daily living, as well as general activities particular to the user's occupation, without interference from the orthotic. This is provided by a biasing component which models the movement of the carpal/metacarpal and distal forearm/carpal joints by employing a unique and innovative spring tensioning arrangement in the form of a plurality of coils to provide continuous, low pressure force opposing rotational movement of the hand about the carpus. The multiple coil arrangement mimics the lengthening and shortening of the distance between the metacarpals and the distal ulna-radius as the hand moves volarly and dorsally. By mimicking this lengthening and shortening which has been observed empirically, the biasing component accurately tracks hand movement. It can thus apply a continuous, low level force which accurately opposes rotational movement of the hand about the carpus to promote restoration of normal function to the carpus and forearm. The novel coils of the biasing component are positioned generally on the ulnar side of the carpus where they do not interfere with hand and arm movement during normal activities of daily living. They have a torquing end coupled to the hand and a supporting end which is coupled to the forearm. The biasing component has a rest, or zero force, position in which the hand is slightly and dorsally deviated at an angle from the plane formed by the ulna and radius of the forearm; any volar or dorsal movement from this angle is resisted by the biasing component.

In one embodiment of the invention, the dynamic orthotic appliance consists of three components—a biasing component, a forearm component, and a palmar component. The palmar component is positioned on the ulnar side of the hand and is designed to allow unobstructed flexion of the fingers and opposition of the thumb with the fingers; it couples the supporting end of the biasing component to the hand. The forearm component couples the supporting end of the biasing component to the forearm and maintains the biasing component in particular relationship and alignment with the ulnar aspect of the forearm and carpus during all normal movements. The forearm component allows supination and pronation of the forearm without binding of the appliance or obstructing free movement by creating two independently moving portions, which are generally associated with the distal and proximal aspects of the dorsal forearm to permit differential movement of portions of the forearm during supination and pronation. It places the biasing force on the ulnar side of the forearm and hand in order to avoid interference with normal movement. The three components are articulated in a novel manner which further avoids interference with the normal activities of daily living.

In an alternative embodiment, the device made according to the invention comprises a forearm component having two independently moving portions which are generally associated with the radial and ulnar aspects of the dorsal forearm to permit differential movement of portions of the forearm during supination and pronation. The force exerted by the biasing component can be controlled by a volar transverse strap.

In still another alternative embodiment, the device made according to the invention comprises a forearm component which has been reduced to a simple carpal cuff for stabilization of the biasing device and for providing a fulcrum about which the biasing component rotates. The level of force exerted by the biasing component can be controlled by a transverse strap connected to the supporting end of the biasing component and running volarly from the radial side to the ulnar side of the forearm to removably connect to the surface of the carpal cuff.

The present invention will now be described with reference to the following drawings, in which like reference numbers denote the same element throughout.

BRIEF DESCRIPTION OF THE DRAWINGS

FIG. 16 shows a plan view of the radial side of the forearm component of an alternative embodiment of the dynamic splint with its major topological features.

FIG. 17 shows a plan view of the ulnar side of the forearm component of an alternative embodiment of the dynamic splint with its major topological features.

Figure 1:
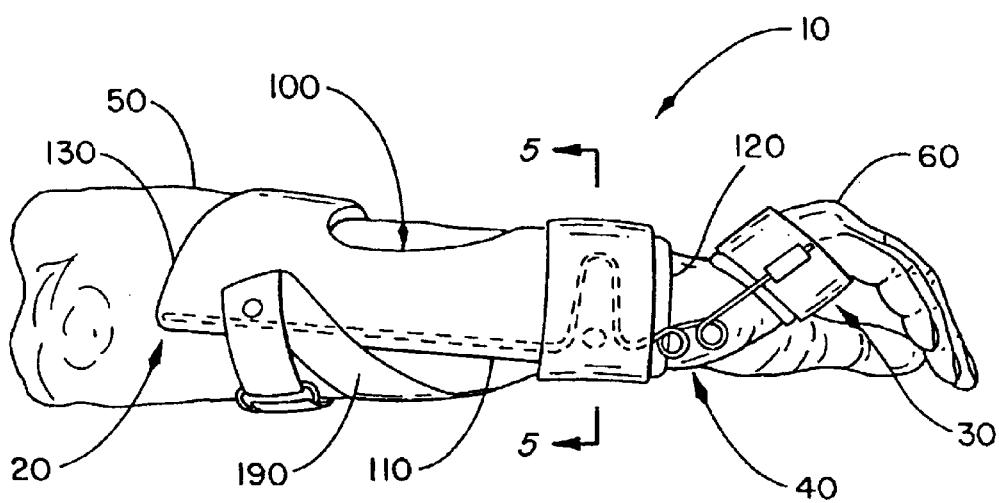
FIG. 1 shows a elevation view of the ulnar aspect of an embodiment of the dynamic splint as it relates to the right arm in accordance with the present invention with its major topological features, with the hand shown in a position where the spring is at a neutral position and not applying tension against the hand.

It is to be understood that the present invention is not limited in its application to the details of construction and arrangement of parts illustrated in the accompanying drawings, since the invention is capable of other embodiments, and of being practiced or carried out in various ways within the scope of the claims. Also, it is to be understood that the phraseology and terminology employed herein are for the purpose of description and not of limitation.

DESCRIPTION OF EMBODIMENTS OF THE INVENTION

The present invention defines methods and appliances for relieving the effects of carpal tunnel syndrome. While several terms have been previously defined heretofore, the terminology to be used in the subsequent detailed description will now be set forth as an aid for those who may not be familiar with these terms as used by the inventor. The terms "volar" and "dorsal" indicate directions of movement or location, where a volar movement is in the direction of the palm of the hand and dorsal movement is in the direction of the back of the hand. Similarly the terms can indicate position, where, for example, a volar carpal ligament would be a ligament located in the carpal complex on the palmar side of the hand. The terms "proximal" and "distal" relate to the position of the described object with relationship to the trunk of the body. Thus, the radius and ulna each has a proximal end (the elbow area) and a distal end (the wrist end). Similarly the carpus is composed of a proximal carpal row of five bones and a distal carpal row of five bones, where the proximal carpal row adjoins the distal end of the radius and ulna. "Supination" is defined as a rotational movement of the radius and ulna which results in a palm up position of the hand, whereas "pronation" is defined as a similar rotational movement resulting in a palm down position of the hand. "Dorsiflexion' is defined as a movement of the hand which forms an arc by extending the wrist dorsally. "Cocontraction" is defined as the interaction between the flexor muscle tendons of the volar forearm acting on the wrist, fingers and thumb, with the dorsal extensor muscle tendons of the forearm, to stabilize the same members of the wrist and hand, thus tending to hold the carpal joint in a fixed and stable position.

"Glide" is a term used to describe an involuntary movement of the carpal metacarpal complex, whereby the proximal carpal row is said to glide in a shear manner which maintains a parallel relationship with the distal forearm. A volar glide is observed when, with the fingers extended, the palmar plane has moved in a volar direction with relationship to the distal forearm carpal joint, such movement consisting of a shear movement in a volar direction of the proximal carpal row. The magnitude of volar glide is indicative of the severity of CTS. Similarly, a dorsal glide is observed when the dorsal plane of the hand is moved dorsally through a shear movement of the distal forearm carpal joint, an opposite movement of volar glide. "Ulnar deviation" is defined as a movement of the hand in an ulnar direction without either dorsal or volar movement; the plane of ulnar movement is perpendicular to that of dorsal-volar movement. "Radial deviation" is defined as a movement of the hand in a radial direction opposite to that of ulnar deviation.

Attention is now directed to FIG. 1. The principles set forth in accordance with the present invention are exemplified by the embodiment of a dynamic splint appliance (this particular embodiment is generally designated by the numeral 10) for use in the treatment and prevention of CTS. The splint appliance 10 consists of a forearm component 20, a palmar component 30, and a biasing component 40 and is shown configured in FIG. 1 to the right forearm 50 and right hand 60 of a user with carpal tunnel syndrome. While subsequent descriptions will for consistency and clarity be directed towards use of the appliance 10 with the right forearm of a user, it should be understood that the same appliance can be used on the left forearm and hand of a user, with all elements of the appliance being mirror images of those elements for the right forearm and hand.

Figure 2:
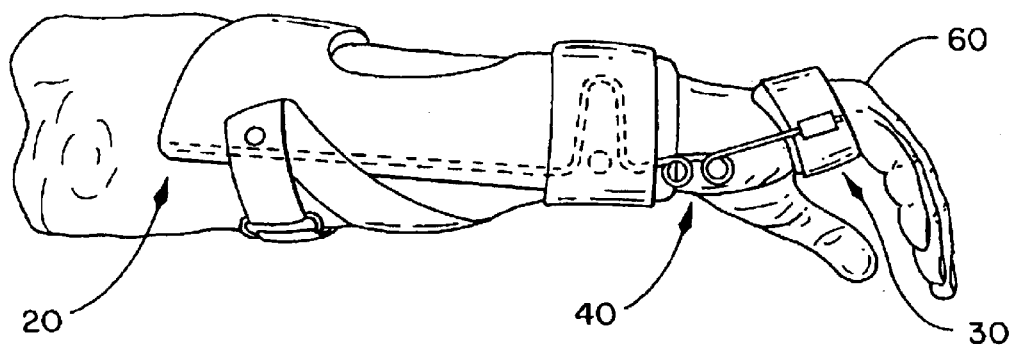
FIG. 2 shows the same elevation view of the dynamic splint as in FIG. 1, but with the spring applying dorsal tension against a volar movement of the hand.
Figure 3:
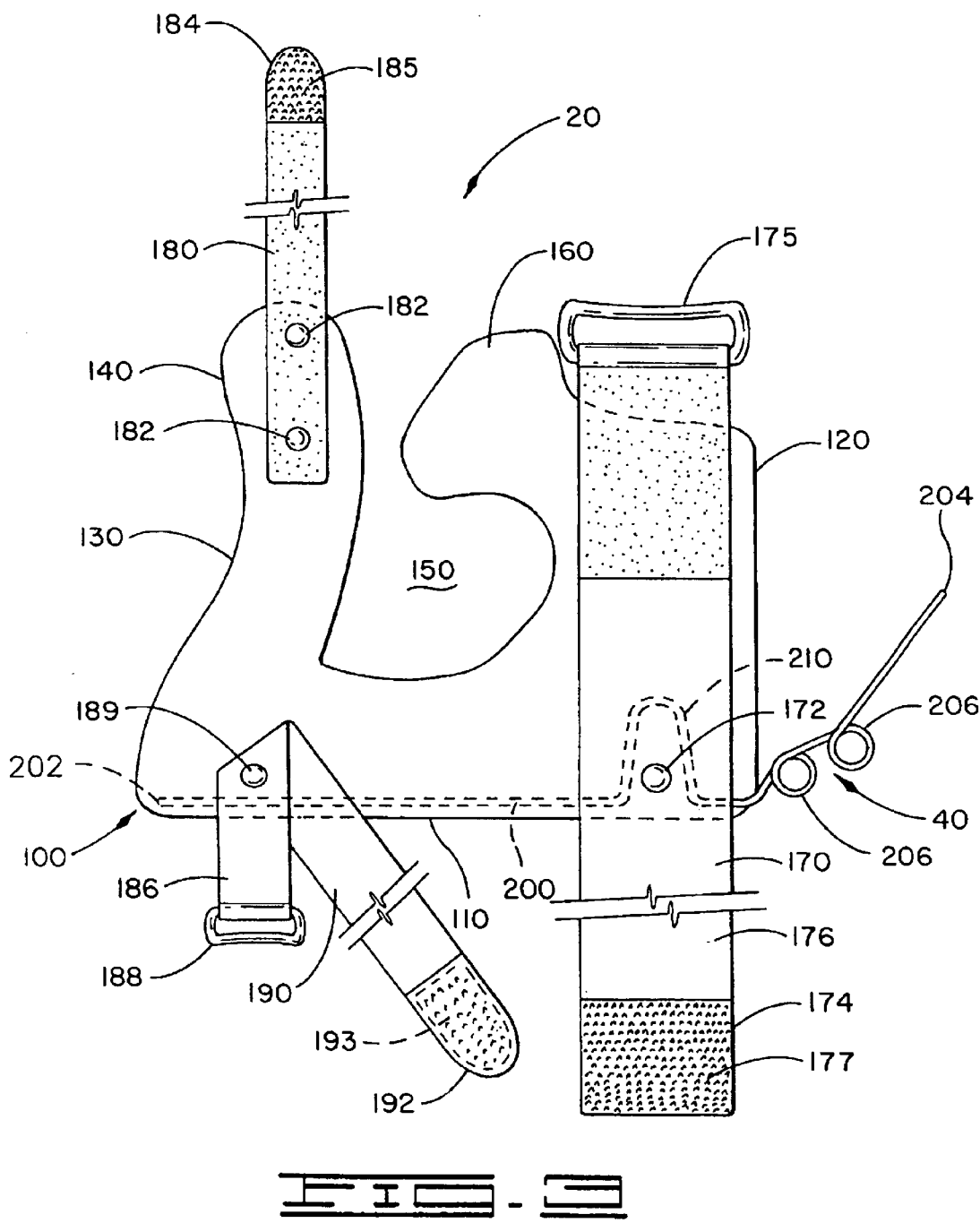
FIG. 3 shows a plan view of the forearm component of an embodiment of the dynamic splint illustrated in FIG. 1. with its major topological features.
Figure 4:
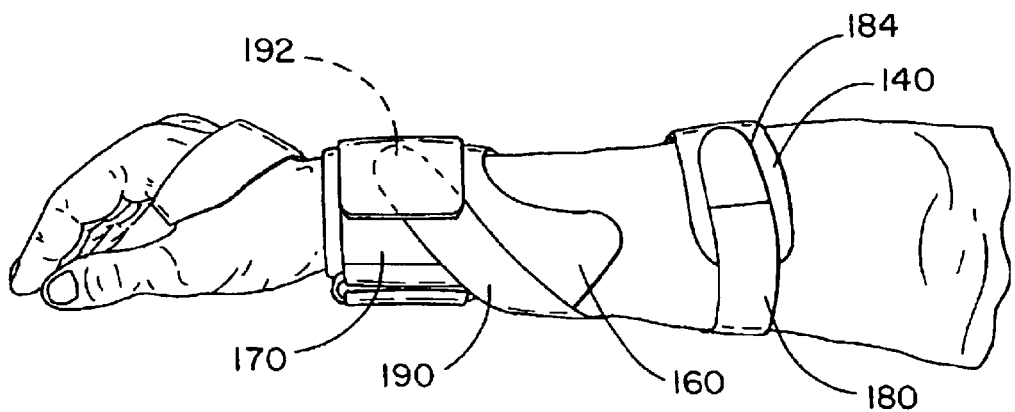
FIG. 4 shows an elevation view of the radial aspect of the dynamic splint as it relates to the right arm in accordance with the present invention.

The forearm component 20 of splint appliance 10 is shown more generally in FIGS. 1, 2, and 4. The forearm component 20 is configured as a generally semicircular splint body 100 shown contoured around the dorsal side of the forearm 50 in FIG. 1 and in a flattened plan in FIG. 3. The splint body 100 is oriented on the forearm 50 with its distal edge 120 generally covering the distal radius and ulna, its proximal edge 130 in the direction of the elbow, and its ulnar edge 110 oriented so that it is generally parallel to the ulna (not shown) of forearm 50. The proximal strap support 140 and the transverse strap fulcrum 160 are wrapped over the dorsum of the forearm 50 so that both extend to points generally adjacent to the radius bone of the forearm 50, so as to capture only the dorsum of the forearm 50.

Supination and pronation of the forearm ordinarily cause the biasing component to bind and the forearm component to buckle at the dorsum of the forearm. Cutout 150 on the dorsum of splint body 100 is provided to solve the binding problem. It is generally centered on the dorsum of the forearm 50 and functions to prevent binding of the appliance during supination and pronation. Allowing the distal and proximal ends of splint 100 to move relatively independently of each other while being connected only along the ulnar edge 110 provides a two point stabilization of the ulnar edge 110 during supination and pronation and maintains alignment of the ulnar edge 110 along the ulnar side of the forearm. The proximal edge 130 of splint body 100 is convexly contoured on forearm 50 along the dorsum towards the distal radial end and away from the proximal radial end so that the extensor muscle group of the forearm is left uncovered and ergonomically accommodated without binding.

Splint body 100 consists of a thin metal core material cut to the shape seen in FIG. 3 and enclosed by a covering material composed of a neoprene external nylon or other anti-perspiration material, such material as is in common use and knowledge among physical therapists, so that the splint body 100 can be molded and customized to individual forearms and trimmed to accommodate individual differences in forearm length and circumference. The exterior of the covering material should is sensitive to attachment by the hook component of an industry standard hook-and-loop system of the type sold under the trademark "VELCRO", so that transverse strap 190 can be removably attached to appropriate areas of the splint body 100, as described below.

Splint body 100 is secured to the forearm 50 by distal forearm strap 170, proximal forearm strap 180, and transverse strap 190. Distal forearm strap 170 is secured to the splint body 100 by one or more rivets 172, of which a single representation is shown. The rivet 172 as shown also serves to prevent the biasing component 40 from significant movement either distally or proximally along the ulnar side of the forearm. Distal forearm strap 170 is of sufficient length to allow end 174 having an attached hook and loop fastener strip 177 to be brought around the ulnar side of the forearm, across the distal end of the volar forearm, and over the radial forearm, where end 174 passes through distal buckle 175 and back onto distal forearm strap 170, where a cooperating hook and loop fastener strip (not shown) is fixed so that end 174 is removably secured to distal forearm strap 170.

Proximal forearm strap 180 is secured to the proximal strap support 140 by one or more rivets 182. Proximal forearm strap 180 is of sufficient length to allow end 184 having an attached hook and loop fastener strip 185 to be passed around the radial side of the forearm, across the proximal end of the volar forearm, and over the ulnar forearm, where end 184 passes through proximal buckle 188 and back onto proximal forearm strap 180, where a cooperating hook and loop fastener strip (not shown) is fixed so that end 184 is removably secured to proximal forearm strap 180. As shown in this embodiment, proximal buckle 188 is fixedly attached to the fixed end 186 of transverse strap 190 which is fastened to the splint body 100 by rivet 189. However, two separate straps could be employed and fastened with separate rivets as required.

Transverse strap 190 is secured to the splint body 100 by rivet 189. As seen from FIGS. 1 and 4, transverse strap 190 follows a line from the proximal ulnar edge of the splint body, across the volar forearm, and over the transverse strap fulcrum 160, where end 192 having a hook and loop fastener strip 193 is removably secured to the distal strap 170 at an arbitrary point, either by using a cooperating hook and loop fastening strip (not shown) or preferably by attachment directly to the material comprising the distal strap 170 which is sensitive to attachment by the hook component of a standard hook-and-loop fastening means. Transverse strap 190 moves to a limited extent across the transverse strap fulcrum 160, a portion of splint body 100 which provides a platform for transverse strap 190 against the forearm and prevents it from rubbing or binding during supination and pronation. Because of a differential rotation between the distal end and the proximal ends of the forearm during supination/pronation, the transverse strap 190 tends to stabilize the splint body 100 by translating this differential rotation motion to the ulnar edge 110, thus maintaining alignment of the ulnar edge 110 with the ulna.

Figure 5:
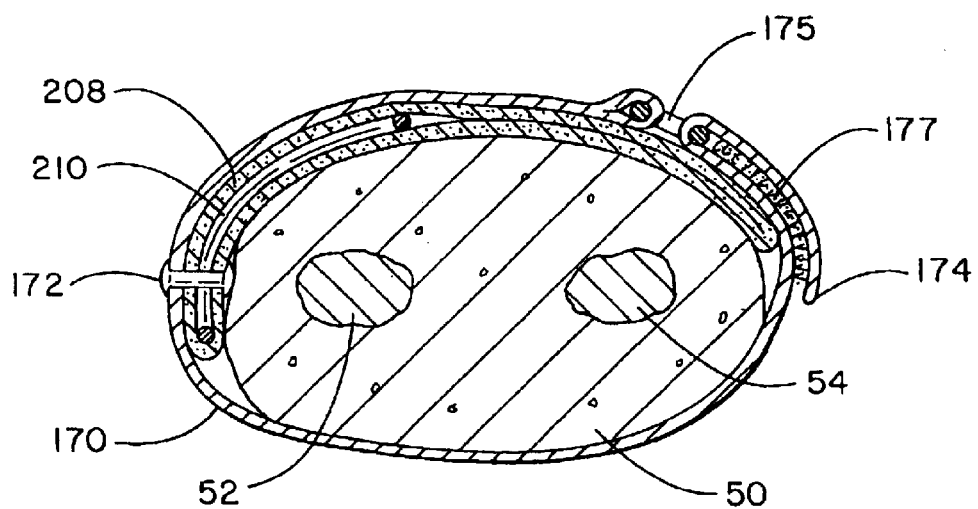
FIG. 5 shows a sectional view of the splint and forearm, illustrating the stabilizing mechanism used for positioning the spring along the ulnar side of the forearm.

Referring to FIGS. 1, 3, and 5, the biasing component 40 of splint appliance 10 is constructed of a formed wire 200 having a supporting end 202 and a torquing end 204. The formed wire 200 is preferably made from a length of 24 gauge 304 stainless steel with a B2 finish, as is commonly known to physical therapists and orthotists in the construction of orthopedic appliances. Other compositions of wire may be used in the fabrication of formed wire 200 without departing from the scope of the invention. A plurality of spring loops 206 are formed near the torquing end 204 with each loop comprised of one or more turns of wire as needed to produce a suitable tensioning force at the torquing end 204, preferably about 8 pounds. It has been found that the multiple loops 206 mimic rotational movement of the hand about the carpus and apply a uniform and continuous force throughout the range of such motion. Formed wire 200 is enclosed in the covering material 208 along the ulnar edge 110 of splint body 100, wherein the proximal end of supporting end 202 is allowed to rotate freely within the sheath formed by the covering material as the forearm moves in supination and pronation. Optionally, rivets (not shown) may be placed at the proximal end of the splint body 100 at the ulnar edge 110, wherein the proximal end of the supporting end 202 is captured between the ulnar edge 110 and the rivet and prevented from migrating within the covering material away from the ulnar edge 110. An ulnar saddle 210 is formed in the formed wire 200 and positioned over the distal ulna 52 to rotationally stabilize the formed wire 200 during pronation and supination of the forearm. Rivet 172, around which the ulnar saddle 210 is positioned, serves to stabilize the formed wire 200 from significant proximal or distal movement. As seen more particularly in FIG. 5, the ulnar saddle 210 curves from the ulnar side of the forearm 50 up to a point on the dorsum of the forearm and then back to the plane of the ulnar edge 110 of splint body 100.

The spring loops 206 are formed and positioned along formed wire 200 so that they are located laterally on the ulnar side of the ulnar-radial/metacarpal joint and the intra-metacarpal joint and are not covered by distal strap 170. It is believed that each spring loop 206 models the action of the corresponding joint. This double loop spring arrangement has been found to provide sufficient proximal-distal tolerance to accommodate changing distance between the metacarpals and the distal ulna-radius during flexion and extension of the hand, and it thus prevents binding of the palmar component 30 when connected to the torquing end 204. The torquing end 204 of formed wire 200 is shaped so that, when connected with the palmar component 30 and attached to a hand, the hand at substantially 20° of dorsiflexion does not encounter resistance from the biasing component 40.

Although one type of general loop configuration has been presented, other tensioning shapes may be used to provide resistance to movement of the torquing end of the biasing component and still remain within the scope of the invention, namely, to apply a low force load opposing volar glide over long intervals of time. For example, during testing of the device, an arrangement was formulated (not shown) consisting of slotted bars comprising the support end and torquing end of the biasing component, with a coiled spring wound around a spool, similar to that found in clocks, fixedly connected to the support end. The torquing end rotated about the axis of the coiled spring as the end of the coiled spring applied pressure opposing dorsiflexion. It was found that this arrangement did not track the change in distance between the metacarpals and the distal ulna-radius during flexion and extension of the hand, although this could be accommodated by fashioning a pin in the palmar component that would travel along a slot in the bar comprising the torquing end during flexion. However, a rigid bar of such a configuration would interfere with ulnar and radial deviation during the normal activities of daily living.

It should be noted that normally the range of deviation for a hand is approximately 35° in a radial direction and 45° in an ulnar direction, but much less range is required to achieve the activities of daily living. The biasing component in the form of a shaped wire 200 allows 20° ulnar deviation, but less restriction on radial deviation, thus permitting a more natural movement of the hand.

Figure 6:
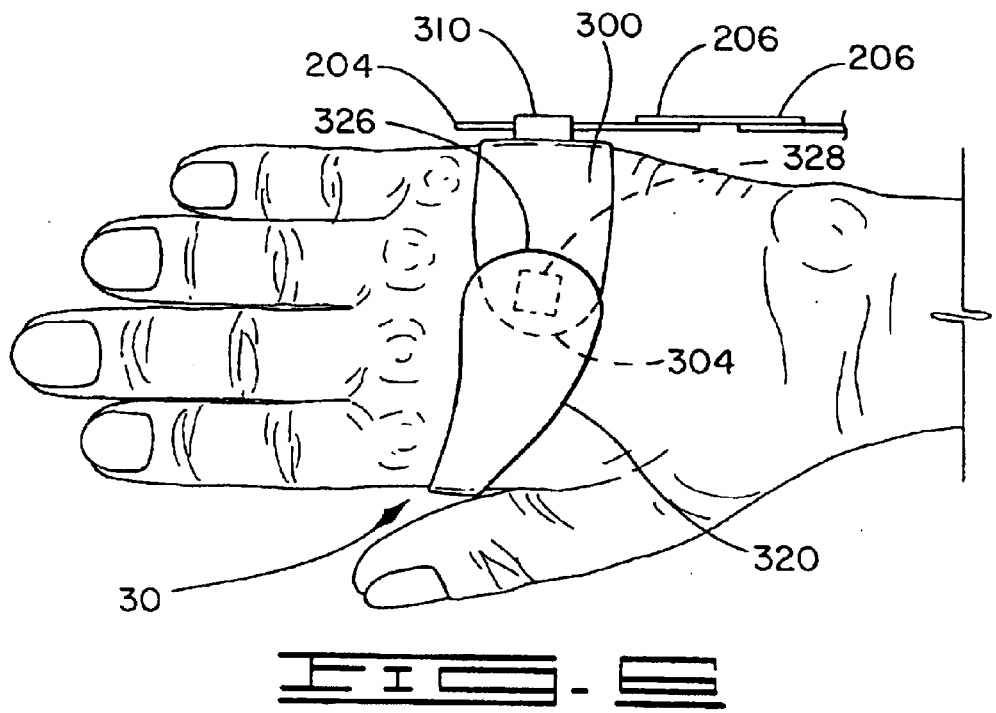
FIG. 6 shows a dorsal view of the hand with the palmar component attached the ulnar side of the hand and the positioning of the springs with relationship to the carpus.
Figure 7:
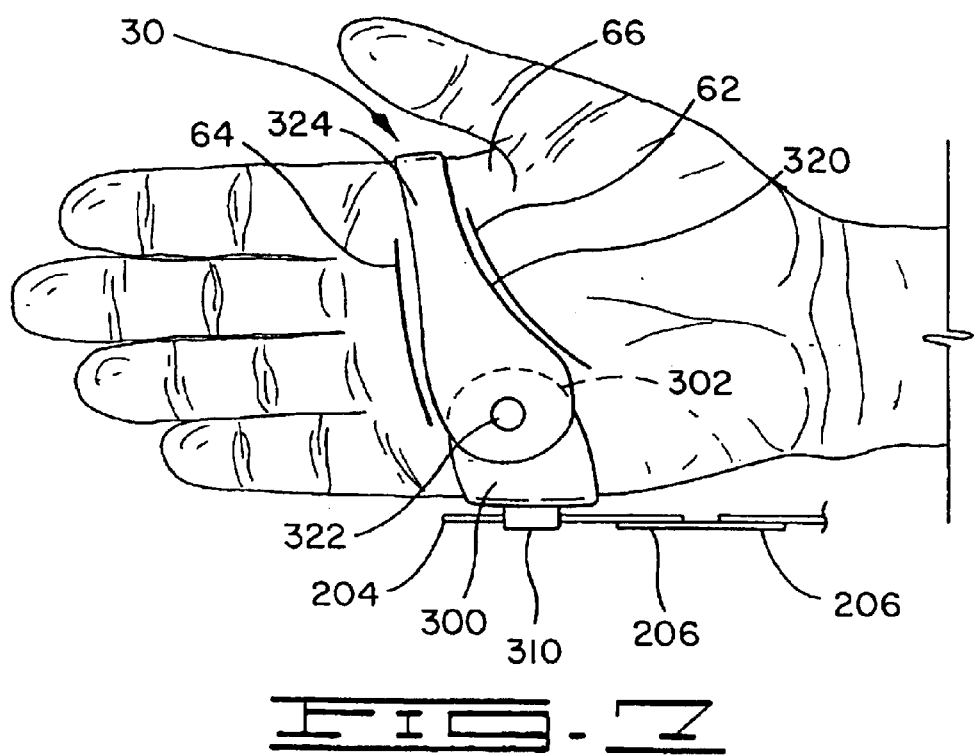
FIG. 7 shows the volar view of the hand with the palmar component attached to the ulnar side of the hand.
Figure 8:
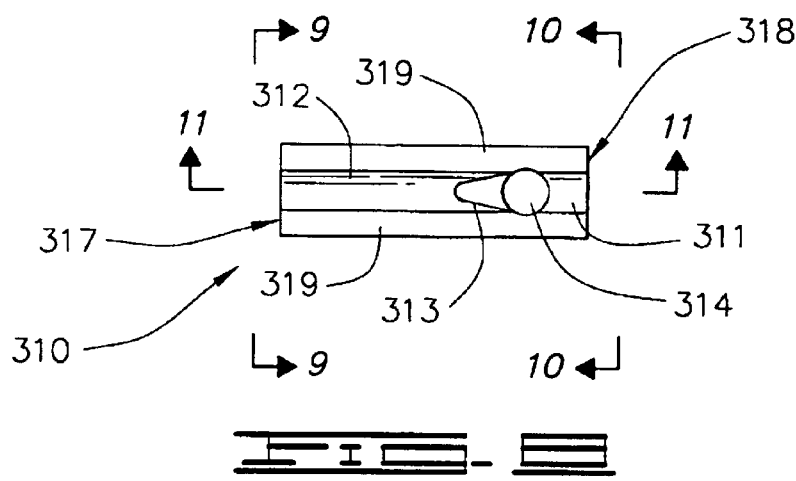
FIGS. 8, 9, and 10 show three views of the connection block used for attaching the spring to the palmar component of the dynamic splint.

Referring now to FIGS. 6 and 7, the palmar component 30 of splint appliance 10 is illustrated as having a rigid ulnar gutter 300 enclosing the ulnar side of the hand and serving as a platform for the fixed attachment of connection block 310. Ulnar gutter 300 is preferably comprised of a plastic material of any suitable composition to enable it to be custom fitted and shaped to the individual hand. Connection block 310 is permanently affixed to ulnar gutter 300 by any suitable means known to the art, including rivets, screws, glue, or capture in a molded channel in ulnar gutter 300. Palm strap 320 is permanently affixed to the volar end 302 of the ulnar gutter 300 by means of a rivet 322, although any suitable means known to the art can be employed. The volar end 302 of ulnar gutter 300 and the volar end 324 of palm strap 320 are shaped so that they are substantially confined between the thenar crease 62 and the MCP joint crease 64 of a typical hand 60 so as to permit unimpeded use of the hand during normal activities of daily living. Palm strap 320 narrows as it passes over the thenar web 66 in order to prevent interference with normal activities. This contouring of palm strap 320 allows unobstructed flexion of the fingers and opposition movement of thumb with that of fingers. The dorsal end 326 of palm strap 320 is removably secured to the dorsal end 304 of the ulnar gutter 300 by cooperating hook and loop attachment strips 328 attached to the palm strap 320 and ulnar gutter 300 by any suitable means. An alternate embodiment (not shown) for palm strap 320 would be to employ the buckling arrangement as described for distal forearm strap 170, while contouring the shape of the strap to accommodate the thenar crease, the MCP joint crease, and the thenar web as described above.

Figures 9, 10:
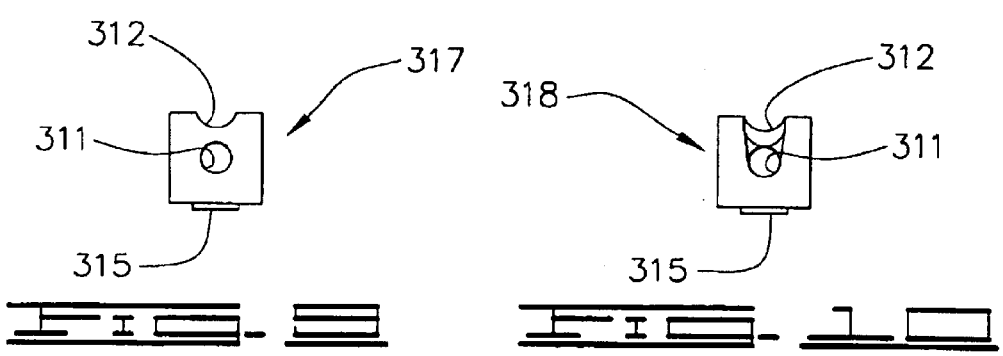
Figure 11:
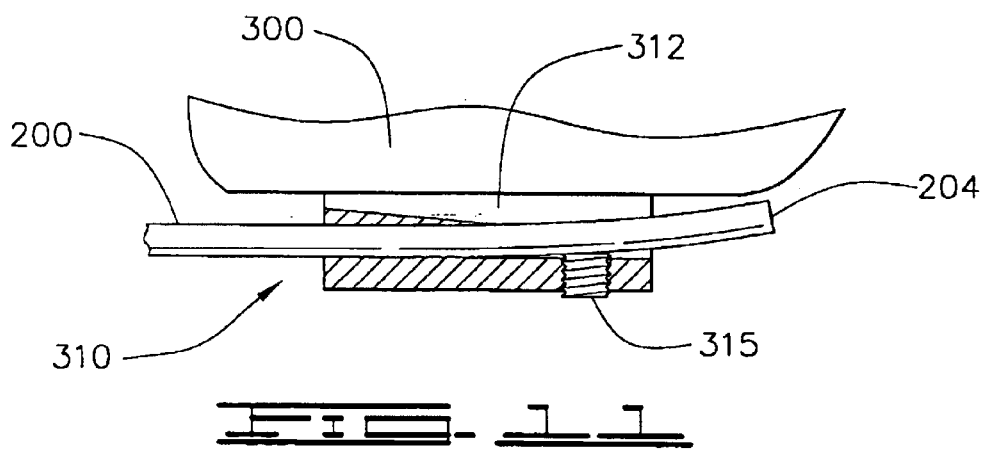
FIG. 11 shows the method of securing the end of the spring to the palmar component of the dynamic splint using the connection block.

The construction of connection block 310 is given in FIGS. 8, 9, 10, and 11. Connection block 310 is formed of a rectangular block of material, preferably of metal composition, having a top side 319 as shown in FIG. 10, a receiving end 317 as shown in FIG. 9, and a clamping end 318 as shown in FIG. 10. Receiving end 317 has a centrally located horizontal bore 311 which is colinear with the longitudinal axis of connection block 310. An inclined bore 312 in the same axial plane as the horizontal bore 311 is slantingly positioned so that at receiving end 317 inclined bore 312 does not intersect horizontal bore 311. Incline bore 312 is slantingly disposed towards the clamping end 318 and horizontal bore 311. Inclined bore 312 gradually approaches horizontal bore 311 so that it intersects horizontal bore 311 forming notch 313, which gradually becomes wider as inclined bore 312 fully intersects and terminates before exiting horizontal bore 311 on its opposite side. Vertical bore 314 intersecting two opposing faces of connection block 310 is perpendicular to the axis of both inclined bore 312 and horizontal bore 311 and is located at the widest point of notch 313. Vertical bore 314 is threaded to receive set screw 315. A dado is formed between the inclined bore 312 and the top side 319 of connection block 310. Top side 319 is fixedly joined to ulnar gutter 300 with its receiving end 317 oriented proximally and its clamping end 318 oriented dorsally as described previously.

During appliance use, the torquing end 204 of formed wire 200 is inserted into the horizontal bore 311 on the receiving end 317 and made to protrude from the clamping end 318. The ulnar gutter 300 is positioned and strapped to the ulnar side of the hand. Set screw 315 is then tightened against formed wire 200 to force formed wire 200 into notch 313 which clamps the connection block 310 to the formed wire 200, so that connection block 310, and consequently the ulnar gutter 300 and the entire palmar component 30, is constrained from rotational movement about formed wire 200 and from longitudinal motion along formed wire 200 by the clamping action of notch 313 on formed wire 200.

The embodiment of the invention illustrated by splint appliance 10 has been described to illustrate one way in which the theory of the invention is implemented in a dynamic orthotic. An alternative embodiment 400 of the invention is shown in FIGS. 12 through 15. This embodiment 400 illustrates how the implementation of biasing component and the solution to prevent binding during supination and pronation can differ from the first embodiment and remain within the scope of the invention.

Figure 13:
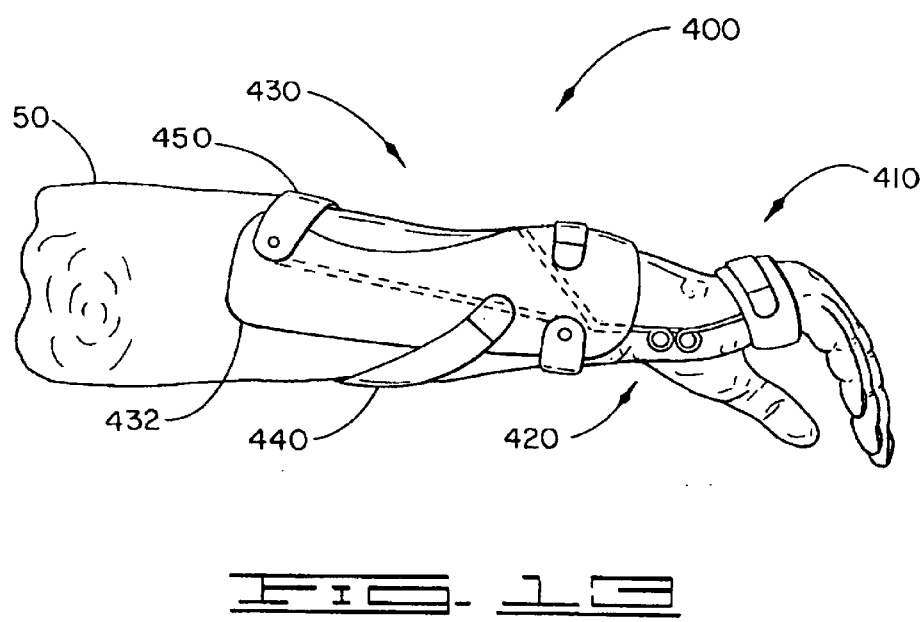
FIG. 13 shows a plan view of the ulnar side of the forearm component of an embodiment of the dynamic splint with its major topological features.
Figure 14:
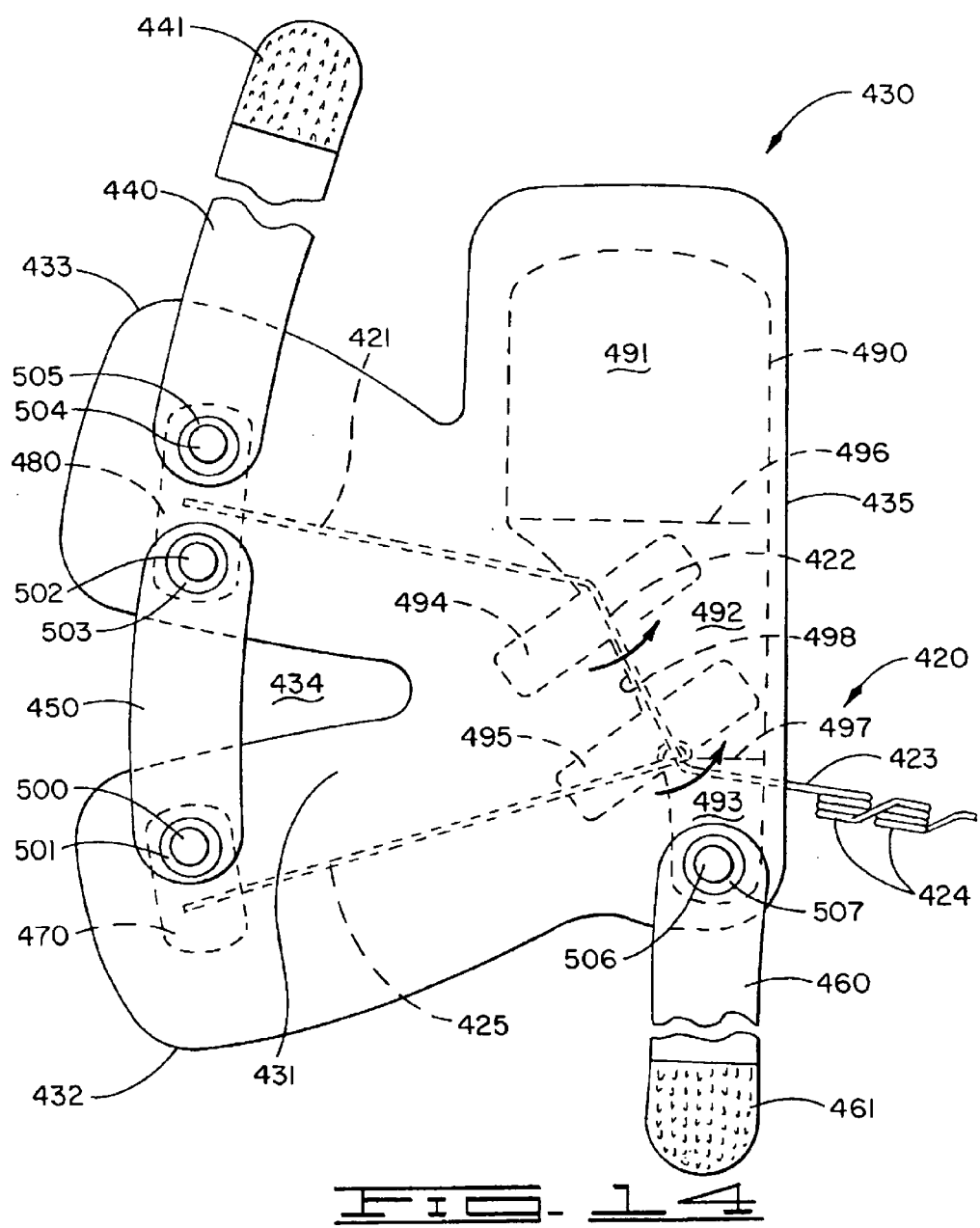
FIG. 14 shows a plan view of the forearm component of an embodiment of the dynamic splint illustrated in FIGS. 12 and 13 with its major topological features.
Figure 15:
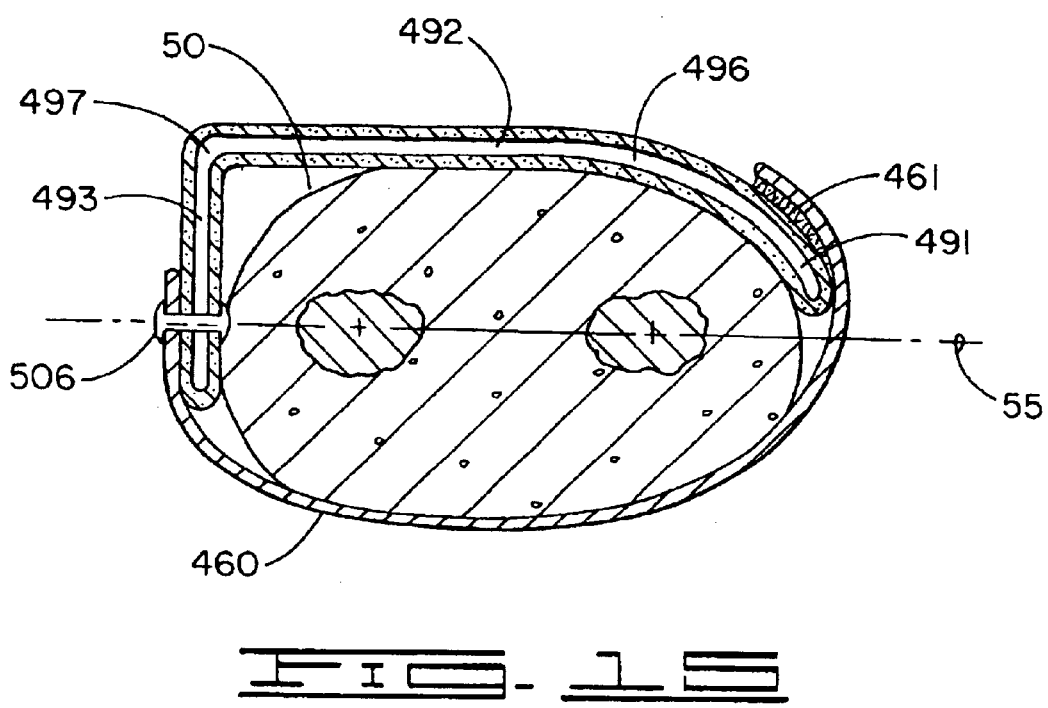
FIG. 15 shows a sectional view of the splint and forearm taken from FIG. 12, illustrating how the dorsal block is employed in an embodiment of the dynamic splint.

Referring to FIGS. 13 and 14 which illustrate in perspective the radial and ulnar aspects, respectively, of the orthotic as it is worn on the right forearm and to FIG. 15 which shows the pattern of the forearm component, an alternative embodiment of the invention consists of splint appliance 400 having a palmar component 410, a biasing component 420, and a forearm component 430. The palmar component 410 is essentially the same as palmar component 30 for splint appliance 10, described previously.

In describing the forearm component 430 of the present embodiment as shown in FIG. 14, it is instructive to compare it with the forearm component 20 of the splint appliance 10 which was presented in the embodiment as shown in FIG. 3. Both figures are oriented in the same manner to the right forearm. The body 431 of splint appliance 400 consists of two pieces of a substantial external nylon or other antiperspiration material, such material as is in common use and knowledge among physical therapists, cut to the shape seen in FIG. 14 and enclosing a core pad of neoprene. Also enclosed within the two layers of covering material are several metal portions which shall be described presently. The covering material is preferably sensitive to attachment by the hook component of an industry standard hook-and-loop system of the type sold under the trademark "VELCRO", so that distal buckle 175 and proximal buckle 188 of the shown as a component of splint appliance 10 can be eliminated and transverse strap 440 and distal carpal strap 460 can be removably attached to appropriate areas of splint body 431, as described below.

The ulnar support plate 470, radial support plate 480, and block plate 490 are sandwiched between the two layers of material composing the splint body 431. Each plate defines a reinforced area on splint appliance 400 to assist strap attachment to body 431 and to position and orient biasing component 420 to the forearm.

Figure 12:
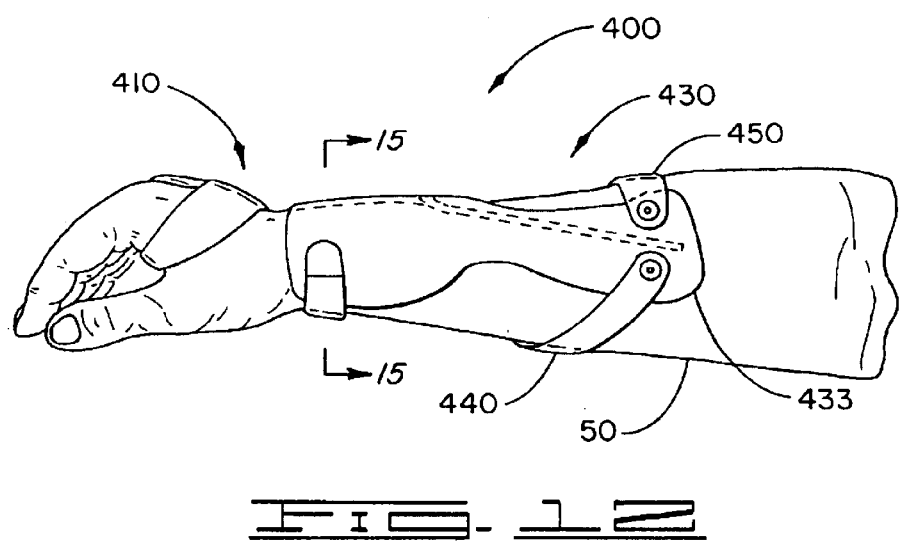
FIG. 12 shows a plan view of the radial side of the forearm component of an embodiment of the dynamic splint with its major topological features.

Ulnar support plate 470 is positioned on the ulnar portion 432 of body 431 and radial support plate 480 is positioned on the radial portion 433 of body 431 and in opposing relation to ulnar support plate 470. Both may be preferably composed of plastic, dead soft aluminum (a term familiar to persons knowledgeable in the art), or some other suitable material which is relatively rigid. Dorsal gap 434 separates the ulnar and radial portions of body 431, with the dorsal strap spanning dorsal gap 434. A first end of dorsal strap 450 is attached to ulnar support plate 470 by means of rivet 500 inserted through washer 501, the outer fabric covering of body 431, ulnar support plate 470, the inner fabric covering of body 431, another washer (not shown), and secured in place in the manner of rivets. A second end of dorsal strap 450 is attached to radial support plate 480 in the same manner as the first end and secured by rivet 502 and washer 503. Dorsal strap 450 is positioned on the dorsum of forearm 50 (FIG. 12). It may be preferably composed of the same material as body 431 and may also contain an expandable portion (not shown) if desired to allow dorsal strap 450 to expand and contract during supination and pronation of forearm 50. It serves to couple the ulnar and radial portions of body 431 to each other in a manner to allow independent movement of said portions without binding but maintaining a general orientation of the portions to forearm 50.

The first end of transverse strap 440 is fixedly attached to radial support plate 480 by means of rivet 504 and washer 505 in the same manner as described previously. The second end of transverse strap 440 has a hook portion 441 sewn thereto and on one side so that it can be wrapped about the volar forearm and attached to the surface of the ulnar distal portion of body 431. Transverse strap 440 corresponds to transverse strap 190 of the first embodiment (FIG. 3), but passes from the radial proximal side of the forearm to the distal ulnar side, rather than from the ulnar proximal side of the forearm to the distal radial side as shown in FIG. 3. Like transverse strap 190, transverse strap 440 stabilizes body 431 by translating differential rotation motion observed in supination and pronation to the radial portion 433 to maintain alignment of radial portion 433 with the radius of forearm 50. In both cases, transverse strap 190, 440 loads the supporting end of the biasing component 40, 420.

Referring again to FIG. 14, block plate 490 is located on the distal edge 435 of splint body 431 and sandwiched between the two layers of material composing the splint body 431. It may be composed of a rigid material which may be appropriately formed, such as plastic, dead soft aluminum, and the like. Its function is to provide support for distal carpal strap 460 and to provide a platform for the biasing component 420. Block plate 490 is comprised of the following three portions: curved portion 491, horizontal portion 492, and vertical portion 493. These portions are shown more clearly in the cross-sectional view shown in FIG. 15. Vertical portion 493 forms an angle approximating ninety degrees with horizontal portion 492 at bend 497; curved portion 491 begins its curvature at bend 496 and continues around the carpus for an arbitrary distance. Block plate 490 may be preferably constructed of dead soft aluminum which permits curved portion 491 to be easily molded to each individual carpus. Horizontal portion 492 is parallel to the plane 55 defined by the centers of the ulna and radius of forearm 50. It has been found by experimentation and measurement that the substantially ninety degree orientation between portions 493 and 492 remains invariant over the range of supination and pronation. Along the angled proximal edge 498 of block plate 490 are two tabs 494 and 495 to accommodate the biasing component which shall be presently described. Tabs 494, 495 are bent back over portion 492 to capture a section of the biasing component 420 therebetween for rotational movement of biasing component 420. The first end of distal carpal strap 460 is fixedly attached to block plate 490 by means of rivet 506 and washer 507 in the same manner as previously described for the first end of the dorsal strap. The second end of distal carpal strap 460 has a hook portion 461 sewn thereto and on one side so that it can be wrapped about the carpus and attached to the surface of the distal portion of body 431 to hold body 431 in close contact and orientation with the forearm.

The biasing component 420 of the splint appliance 400 is illustrated in FIG. 14. It is comprised of spring wire and divided into a torquing end 423, a middle segment 422, and a support end 421, with middle segment 422 and support end 421 being sandwiched between the two layers of fabric comprising the splint body 431 and with torquing end 423 exposed. The wire is preferably 24 gauge 304 stainless steel with a B2 finish, as is commonly known to physical therapists in the construction of orthopedic appliances. Other compositions of wire may be used in the fabrication of biasing component 420 without departing from the scope of the invention. Torquing end 423 extends from the within body 431 to attach to the palmar component 410 in the same manner as described previously. Along its extent are two spring loops 424 positioned along the wire so that they are located laterally on the ulnar side of the distal forearm/carpal joint and the carpal/metacarpal joint and slightly dorsal to the axis of the carpus. The two spring loops 424 may optionally be enclosed in a pouch (not shown) composed of the same material comprising the splint body 431 in order to prevent chafing of the ulnar side of the hand and to provide a comfortable pad. Middle segment 422 is loosely captured by tabs 494, 495 on block plate 491 so that torquing end 423 may swing vertically along portion 493 of block plate 491 without binding. Middle segment 422 is positioned to rotationally stabilize and maintain the position of the formed wire comprising the biasing component 420 during pronation and supination of the forearm. Support end 421 extends along the radial side of forearm 50 so that its end is captured between radial support plate 480 and the outer layer of fabric comprising body 431. Support end 421 may be bent slightly from the plane formed by torquing end 423 and middle segment 422 to better conform to the radial side of the forearm. To additionally stabilize the biasing component 420, an ulnar arm 425 formed of spring wire is loosely attached to the wire at the apex of the angle formed by the torqueing end 423 and middle segment 422 by means of a simple loop in its end. The opposite end of ulnar arm 425 is captured between ulnar support plate 470 and the outer layer of fabric comprising body 431.

As an example of a specific embodiment for the invention, the distance between the proximal spring loop 424 and the bend between middle segment 422 and the torqueing end 423 is preferably 0.65 inches for the implementation shown for embodiment 400. The obtuse angle between the middle segment 422 and torquing end 423 is preferably between 125° and 130°, and the angled proximal edge 498 of block plate 490 should therefore mirror this angle. The obtuse angle between the middle segment 422 and support end 421 is preferably between 125° and 135°. It should be understood that these values are presented for example and may vary slightly depending upon the individual.

Figure 18:
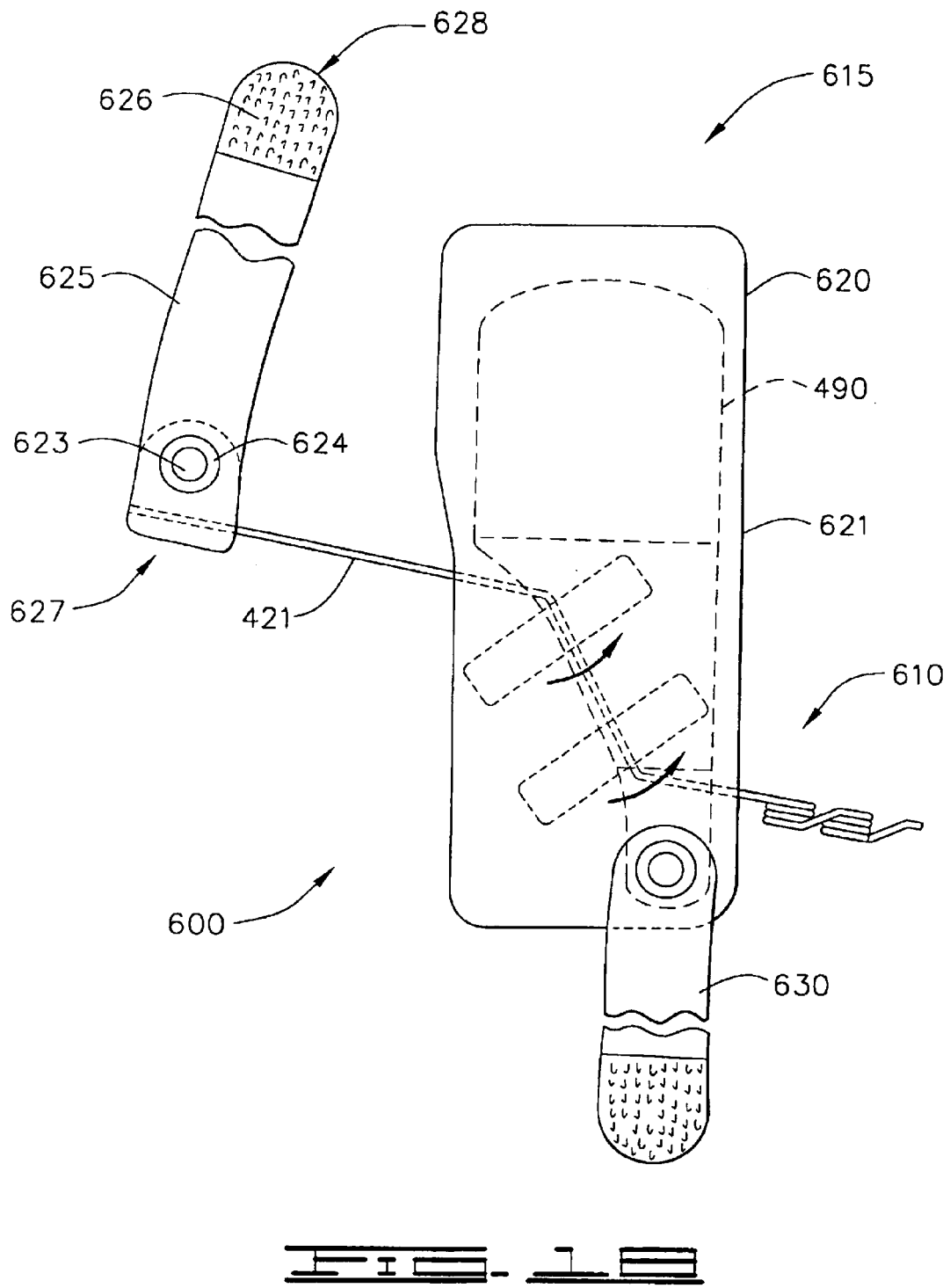
FIG. 18 shows a plan view of the forearm component of an alternative embodiment of the dynamic splint illustrated in FIGS. 16 and 17 with its major topological features and illustrating the removal of portions of the forearm component.

Still another embodiment 600 of the invention is shown in FIGS. 16, 17, and 18. This embodiment 600 illustrates an alternate implementation of the forearm component which illustrates how the forearm component can be reduced to a simple carpual cuff for supporting the biasing component and maintaining alignment of the biasing component with the ulnar side of the hand.

Referring to FIGS. 16 and 17 which illustrate in perspective the radial and ulnar aspects, respectively, of the orthotic as it is worn on the right forearm 50, and to FIG. 18 which shows the pattern of the forearm component, an embodiment 600 of the invention is illustrated as a splint appliance having a palmar component 605, a biasing component 610, and a forearm component 615. The plan view of the forearm component 615 of the present embodiment 600 is shown in FIG. 18 and is oriented in a similar manner to the embodiments shown in FIGS. 3 and 14 for comparison purposes. In this embodiment 600, each of the components—the forearm component 615, the biasing component 610 and the palmar component 605—differs from similar components in other embodiments described herein.

The forearm component 615 of this embodiment 600 comprises a carpal cuff 620 and a transverse strap 625. The carpal cuff 620 consists of two pieces of a substantial external nylon or other anti-perspiration material, such material as is in common use and knowledge among physical therapists and orthotists, cut to the shape seen in FIG. 18 and enclosing a core pad of neoprene. The covering material is preferably sensitive to attachment by the hook component of an industry standard hook-and-loop system of the type sold under the trademark "VELCRO", so that transverse strap 625 and distal carpal strap 630 can be removably attached to appropriate areas of carpal cuff 620, as described below. Block plate 490 (described previously and shown in FIGS. 14 and 15) is located on the distal edge 621 of carpal cuff 620 and sandwiched between the two layers of material composing the carpal cuff 620 to position and orient biasing component 610 to the forearm 50. Its function is to provide support for distal carpal strap 630 and to provide a fulcrum and stabilization for biasing component 610. Biasing component 610 of embodiment 600 differs from that of embodiment 400 in that the ulnar arm 425 (FIG. 14) is absent. Otherwise, all other references for the biasing component as shown in FIG. 14 are the same as those shown for biasing component 610 as shown in FIG. 18.

The first end 627 of transverse strap 625 is fixedly attached to the supporting end 421 of biasing component 610 by wrapping it around the free end of supporting end 421 and securing it by means of rivet 623 and washer 624. Other means well known to the art could be used for securing the first end 627 of transverse strap 625 to the supporting end 421 of biasing component 615 without departure from the scope of the invention. The second end 628 of transverse strap 625 has a hook portion 626 sewn thereto and on one side so that it can be wrapped about the volar forearm and attached to the surface of the carpal cuff 620. Transverse strap 625 stabilizes the biasing component 615 and provides stabilization against which volitional force is exerted by the hand against the biasing component 615 by loading the supporting end 421 of biasing component 615. Supporting end 421 may be optionally enclosed in a flexible plastic sheathing material for comfort. Palmer component 605 for embodiment 600 is an extension of the torquing end 423 of biasing component 605, wherein torquing end 423 (FIGS. 16 and 17) is wrapped downwardly across the palm of the hand from the ulnar to the radial side, up the radial side, and back over the dorsum of the hand to form an open loop through which the hand is inserted. This extension of torquing end 423 may be optionally encased in a flexible plastic sheath for comfort for the individual.

The invention is designed to realistically mirror the movement of the hand without interfering with the normal activities of daily living. According to the embodiments of the invention presented herein, the biasing component (40, 420, 610) is positioned by the palmar component and the forearm component to reside laterally on the ulnar side of the distal forearm/carpal joint and the carpal/metacarpal joint, and slightly dorsal to the axis of the carpus. This positioning allows the appliance to correctly track the elliptical path that the hand follows during extension and flexion. It is adjusted by the therapist or at the factory so no force is applied by the biasing component (40, 420, 610) when the palm is at approximately 20° dorsiflexion; this is the neutral, or zero force, position. When the palm is volitionally moved in a volar direction, the biasing component (40, 420, 610) tends to force the palm back to the neutral position at 20° dorsiflexion. This biasing force is resisted by the extensor muscles of forearm 50 which further tends to strengthen the extensors and restore a normal flexor-to-extensor ratio of four to one, which tends to stabilize the carpal-metacarpal joint. At the same time the dorsal attitude of the palm at the zero force position tends to apply a long-term low force against the PTCL which will lengthen the ligament over time and thus relieve the symptoms of CTS.

According to embodiments 400, 600 of the invention, the support end of the biasing component sets the tension of the dual springs at the carpus by tightening or loosening the transverse strap, which loads the springs to the desired tension. This permits the tension on the biasing component to be easily adjusted. Furthermore, the design of the biasing component enables the orthotic to fit more individuals because it will accommodate varying sizes of forearm and wrist. Measurable improvement in the patient's condition should be observed in about three to four weeks of continuous use.

As has been demonstrated, the present invention provides an advantageous method and apparatus for applying dynamic pressure to the transverse carpal, volar carpal, and intra-carpal ligaments, in a matter tending to relieve contractures of these ligaments and thus relieve the pain caused by these contractures. The invention also corrects altered kinematics associated with carpal tunnel syndrome (CTS) by increasing the carpal volume, while simultaneously allowing free movement of the patient's wrist with minimal impediment during activities of daily living. Additionally, the invention provides optional adjustable resistance in either the volar or dorsal direction for reestablishing normal cocontraction of the musculature associated with the carpus.

The embodiments described serve to illustrate obvious modifications which are contemplated within the scope of this invention and the following claims. Additional variations and modifications in those embodiments may occur to those skilled in the art once they learn of the basic inventive concepts. Therefore, it is intended that the appended claims shall be construed to include both the preferred embodiment and all such variations and modifications as fall within the spirit and scope of the invention.

What is claimed is:

1. An orthopedic appliance adapted to be worn on a forearm and a hand of a person exhibiting symptoms of carpal tunnel syndrome, the appliance comprising:

a. a biasing means with a plurality of adjacent coils along its length, each coil having a separate non-coaxial centerline, the biasing means alignable with the ulnar side of the forearm and not with the dorsum of the forearm, the biasing means having a supporting end and a torquing end, the torquing end disposed to apply a continuous, low level force to the hand over time and in a direction encouraging dorsal glide;

b. a palmar component coupling the torquing end to the carpal-metacarpal complex of the hand, the palmar component comprising:

i. an ulnar gutter having a dorsal end and a palmar end, the ulnar gutter being sized and configured to the hand such that the dorsal end extends from the ulnar side of the hand to approximately the midpoint of the dorsal side of the hand and the palmar end extends from the ulnar side of the hand to approximately the midpoint of the palm;

ii. a palmar strap having a fixed end and a attachable end, the fixed end permanently secured to the palmar end of the ulnar gutter, the attachable end passing from the palmar end across the thenar web between the thumb and forefinger to the dorsal end and being removably secured to the dorsal end so as to secure the ulnar gutter firmly to the ulnar side of the hand, and iii. a connection means fixedly attached to the ulnar gutter at a point proximal to the ulnar side of the hand, whereby the torquing end of the biasing means is coupled to the palmar component at a point outboard of the ulnar side of the hand so as not to interfere with normal activities of daily living; and, c. a forearm component sized and configured to be rigidly and removably attached to the forearm, the forearm component providing a stable platform for the supporting end and maintaining alignment of the torquing end with the ulnar side of the carpal-metacarpal complex during movement of the forearm and hand.

2. The orthopedic appliance described in claim 1, wherein the palmar end is confined within the area of the palm delineated by and interior to the thenar crease of the palm and the MCP joint crease of the palm.

3. The orthopedic appliance described in claim 1, wherein the forearm component comprises the following:

a. a splint shell substantially conforming to the dorsum and sides of the forearm, the splint shell having a distal end, a proximal end, an ulnar edge between the distal end and the proximal end, a radial edge between the distal end and the proximal end, and a dorsal portion extending from the distal end to the proximal end and between the radial edge and the ulnar edge; and b. a shell securing means for removably securing the splint shell to the forearm.

4. The orthopedic appliance described in claim 3, wherein the proximal end of the splint shell is recessed to permit unimpeded movement of the extensor muscle group on the dorsal side of the forearm.

5. The orthopedic appliance described in claim 3, wherein the shell securing means comprises a distal forearm strap proximate to the distal end and encircling the distal forearm to removably secure the split shell to the forearm.

6. The orthopedic appliance described in claim 5, wherein the shell securing means further comprises a proximal forearm strap proximate to the proximal end and encircling the proximal forearm to removably secure the split shell to the forearm.

7. The orthopedic appliance described in claim 5, wherein the shell securing means further comprises a first transverse strap extending from a point on the splint shell which is proximate to the proximal end and the ulnar edge transversely across the volar forearm to a point on the splint shell which is proximate to the distal end of the radial edge, the first transverse strap being releasably secured, whereby the first transverse strap maintains alignment of the ulnar edge of the splint shell with the ulna of the forearm during supination and pronation.

8. The orthopedic appliance described in claim 7, wherein the splint shell further comprises a cutout extending from the radial edge a distance into the dorsal portion, the cutout defining a proximal portion and a distal portion connected only along the ulnar edge of the splint shell, whereby the proximal portion can move relatively independently of the distal portion while both the proximal and distal portions maintain alignment of the ulnar edge with the ulna of the forearm during supination and pronation.

9. The orthopedic appliance described in claim 8, further comprising a transverse strap fulcrum portion extending proximally from the distal portion a distance generally along the path of the first transverse strap and along the radial edge, the transverse strap fulcrum portion providing a fulcrum for the first transverse strap during supination and pronation of the forearm.

10. The orthopedic appliance described in claim 3, wherein the forearm component further comprises the following:

a. a dorsal gap on the dorsal portion, the dorsal gap extending distally a distance from the proximal end and terminating a distance from the distal end, the dorsal gap defining an ulnar portion and a radial portion, the ulnar and radial portions each extending a distance from the proximal end of the splint shell and unconnected along the distance; and b. a dorsal strap extending over the dorsum of the forearm and spanning the dorsal gap, the dorsal strap having a first end fixedly connected to the ulnar portion and a second end fixedly connected to the radial portion, whereby the radial and the ulnar portions move independently within the confines of the dorsal strap.

11. The orthopedic appliance described in claim 10, wherein the forearm component further comprises a second transverse strap extending from a point on the splint shell which is proximate to the proximal end and the radial edge transversely across the volar forearm to a point on the splint shell which is proximate to the distal end and the ulnar edge, the second transverse strap being releasably secured, whereby the second transverse strap maintains alignment of the ulnar edge of the splint shell with the ulna of the forearm during supination and pronation.

12. The orthopedic appliance described in claim 11, wherein the biasing means is a continuous wire from which the supporting end and the torquing end are composed with a middle segment therebetween, the torquing end positioned along the ulnar side of the forearm and hand, the torquing end with the adjoining coils fabricated along the length of the torquing end, the adjoining coils positioned laterally to the distal forearm/carpal and the carpal/metacarpal joints and slightly dorsal to the axis of the carpus, the middle segment passing over the dorsum of the forearm, the supporting end positioned along the radial side of the forearm in attachment with the radial portion, the middle segment serving as an axis of rotation for the supporting end and the torquing end, the second transverse strap controlling the dorsal attitude of the torquing end through tension applied to the radial portion and therefore the supporting end.

13. The orthopedic appliance described in claim 12, wherein a first obtuse angle is formed between the middle segment and the supporting end and a second obtuse angle is formed between the middle segment and the torquing end, whereby the torquing end provides both a force resisting volar glide and promoting dorsal glide and simultaneously a slight force promoting ulnar deviation as tension is volarly increased against the supporting end by the second transverse strap.

14. The orthopedic appliance described in claim 1, wherein the biasing means comprises a spring having an axis associated with the supporting end, the spring being undamped, the supporting end attached to the forearm component and alignable with the ulnar side of the forearm while the axis is distally positioned on the ulnar side of the forearm, the torquing end attached to the palmar component to provide torque opposing volar movement of the palmar component at substantially 20° of dorsiflexion or less, the supporting end maintaining orientation of and stabilizing the biasing means along the ulnar aspect of the forearm during supination and pronation.

15. The orthopedic appliance described in claim 14, wherein the axis of the spring is approximately positioned on the ulnar side of the distal forearm/carpal and carpal/metacarpal joints and slightly dorsal to the axis of the carpus, whereby an elliptical arc is formed that maintains placement of the palmar component throughout extension and flexion of the hand.

16. An orthopedic appliance adapted to be worn on a forearm and a hand of a person exhibiting symptoms of carpal tunnel syndrome, the appliance comprising:
   a. a palmar component sized for attachment to the carpal-metacarpal complex of the hand;
   b. a biasing component consisting of a continuous wire having a plurality of adjoining coils formed alone its length with each coil having a separate centerline, the biasing component aligned with the ulnar side of the forearm, the biasing component having a supporting end and a torquing end, the torquing end coupled to the palmar component; and,
   c. a forearm component sized and configured to be rigidly and removably attached to the forearm, the forearm component providing a stable platform for the supporting end and maintaining alignment of the torquing end with the ulnar side of the carpal-metacarpal complex during movement of the forearm and hand, the coils disposed thereby to apply a dorsally-directed force to the hand.

17. The orthopedic appliance described in claim 16, wherein the plurality of adjoining coils are positioned laterally to the distal forearm/carpal and the carpal/metacarpal joints and slightly dorsal to the axis of the carpus.

18. The orthopedic appliance described in claim 16, wherein the forearm component is comprised of:
   a. a splint shell substantially conforming to the dorsum and sides of the forearm, the splint shell having a distal end, a proximal end, an ulnar edge between the distal end and the proximal end, a radial edge between the distal end and the proximal end, and a dorsal portion extending from the distal end to the proximal end and between the radial edge and the ulnar edge; and,
   b. a shell securing means for removably securing the splint shell to the forearm.

19. The orthopedic appliance described in claim 18, wherein the splint shell is composed of a semi-rigid material.

20. The orthopedic appliance described in claim 18, wherein the shell securing means comprises a first transverse strap extending from a point on the splint shell which is proximate to the proximal end of the ulnar edge transversely across the volar forearm to a point on the splint shell which is proximate to the distal end of the radial edge, the first transverse strap being releasably secured, whereby the first transverse strap maintains alignment of the ulnar edge of the splint shell with the ulna of the forearm during supination and pronation.

21. The orthopedic appliance described in claim 20, wherein the splint shell further comprises a cutout extending from the radial edge a distance into the dorsal portion, the cutout defining a proximal portion and a distal portion connected only along the ulnar edge of the splint shell, whereby the proximal portion can move relatively independently of the distal portion while both the proximal and distal portions maintain alignment of the ulnar edge with the ulna of the forearm during supination and pronation.

22. The orthopedic appliance described in claim 21, further comprising a transverse strap fulcrum portion extending proximally from the distal portion a distance generally along the path of the first transverse strap and along the radial edge, the transverse strap fulcrum portion providing a fulcrum for the first transverse strap during supination and pronation of the forearm.

23. The orthopedic appliance described in claim 18, wherein the shell securing means comprises a second transverse strap extending from a point on the splint shell which is proximate to the proximal end and the radial edge transversely across the volar forearm to a point on the splint shell which is proximate to the distal end and the ulnar edge, the second transverse strap being releasably secured, whereby the second transverse strap maintains alignment of the ulnar edge of the splint shell with the ulna of the forearm during supination and pronation.

24. The orthopedic appliance described in claim 23, wherein the forearm component further comprises the following:
   a. a dorsal gap on the dorsal portion, the dorsal gap extending distally a distance from the proximal end and terminating a distance from the distal end, the dorsal gap defining an ulnar portion and a radial portion, the ulnar and radial portions each extending a distance from the proximal end of the splint shell and unconnected along the distance; and
   b. a dorsal strap extending over the dorsum of the forearm and spanning the dorsal gap, the dorsal strap having a first end fixedly connected to the ulnar portion and a second end fixedly connected to the radial portion,
   whereby the radial and the ulnar portions move independently within the confines of the dorsal strap.

25. The orthopedic appliance described in claim 24, wherein the biasing component further comprises a middle segment connecting the supporting end and the torquing end, the torquing end positioned along the ulnar side of the forearm and hand, the middle segment passing over the dorsum of the forearm, the supporting end positioned along the radial side of the forearm in attachment with the radial portion, the middle segment serving as an axis of rotation for the supporting end and the torquing end, the second transverse strap adjustably controlling the dorsal attitude of the torquing end through tension applied to the radial portion and therefore the supporting end.

26. The orthopedic appliance described in claim 25, wherein a first obtuse angle is formed between the middle segment and the supporting end and a second obtuse angle is formed between the middle segment and the torquing end, whereby the torquing end provides a force resisting volar glide and promoting dorsal glide and simultaneously a slight force promoting ulnar deviation as tension is volarly increased against the supporting end by the second transverse strap.

27. The orthopedic appliance described in claim 16, wherein the palmar component is an extension of the torquing end of the biasing component, wherein the extension encircles the hand.

28. An orthopedic appliance adapted to be worn on a forearm and a hand of a person exhibiting symptoms of carpal tunnel syndrome, the appliance comprising:
   a. a palmar component sized for attachment to the carpal-metacarpal complex of the hand, the palmar component comprising:
      i. an ulnar gutter having a dorsal end and a palmar end, the ulnar gutter being sized and configured to the hand such that the dorsal end extends from the ulnar side of the hand to approximately the midpoint of the dorsal side of the hand and the palmar end extends from the ulnar side of the hand to approximately the midpoint of the palm;

ii. a palmar strap having a fixed end and a attachable end, the fixed end permanently secured to the palmar end of the ulnar gutter, the attachable end passing from the palmar end across the thenar web between the thumb and forefinger to the dorsal end and being removably secured to the dorsal end so as to secure the ulnar gutter firmly to the ulnar side of the hand, and iii. a connection means fixedly attached to the ulnar gutter at a point proximal to the ulnar side of the hand;

b. a biasing component aligned with the ulnar side of the forearm, the biasing component formed of a continuous wire with a supporting end and a torquing end, the torquing end coupled to the connection means of the ulnar gutter, the torquing end with a plurality of adjacent coils along its length, each coil having a separate non-coaxial centerline; and, c. a forearm component sized and configured to be rigidly and removably attached to the forearm, the forearm component providing a stable platform for the supporting end and maintaining alignment of the torquing end with the ulnar side of the carpal-metacarpal complex during movement of the forearm and hand, the coils disposed thereby to apply a dorsally-directed force to the hand.

29. A method of relieving the pain associated with carpal tunnel syndrome and increasing the carpal volume through use of an appliance sized and configured to a forearm and a hand of an individual person manifesting pain, the appliance having a forearm component, a palmar component, and a biasing component with a supporting end, a torquing end, and a plurality of adjacent coils formed therebetween, each coil having a separate non-coaxial centerline, the method operating to relieve contractatures of the volar carpal ligaments and to restore the cocontraction ratio between the flexor and extensor muscle tendons of the forearm, without interfering with normal activities of daily living, the method comprising the steps of a. releasably attaching the forearm component in fixed relation to the dorsal side of the forearm, the forearm component serving to position the supporting end of the biasing component in fixed relationship to the ulnar side of the forearm;

b. releasably attaching the palmar component of the appliance in fixed relationship to the ulnar side of the hand associated with the forearm upon which the forearm component is positioned, so that the palmar component permits free movement of the hand during normal activities of daily living;

c. fixedly connecting the torquing end of the biasing component to the palmar component;

d. positioning the coils of the biasing component adjacent to the ulnar side of the ulnar-radial/metacarpal and intra-metacarpal joints;

e. adjusting the biasing component to support the hand at about 20° dorsiflexion where no force is exerted upon the metacarpal complex of the hand by the biasing component;

f. adjusting the biasing component to provide low level resistance against dorsally- or volarly-directed volitional hand movement diverging from the about 20° dorsiflexion point, wherein dorsal glide is promoted and volar glide is discouraged;

g. maintaining alignment of the biasing component in the position on the ulnar side of the ulnar-radial/metacarpal and intra-metacarpal joints during supination and pronation of the forearm and during ulnar/radial deviation of the carpal-metacarpal complex; and h. permitting unobstructed flexion of the fingers and opposition of the thumb with the fingers.

* * * * *